United States Patent
Sugimoto et al.

(10) Patent No.: US 9,456,971 B2
(45) Date of Patent: Oct. 4, 2016

(54) MOISTURIZER AND COSMETIC AGENT CONTAINING SAME

(71) Applicant: AJINOMOTO CO., INC., Tokyo (JP)

(72) Inventors: Takanori Sugimoto, Kanagawa (JP); Nana Haraya, Kanagawa (JP); Masatoshi Saito, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/584,310

(22) Filed: Dec. 29, 2014

(65) Prior Publication Data
US 2015/0111859 A1    Apr. 23, 2015

Related U.S. Application Data

(63) Continuation of application No. PCT/JP2013/068257, filed on Jul. 3, 2013.

(30) Foreign Application Priority Data

Jul. 3, 2012  (JP) .................... 2012-149015

(51) Int. Cl.
| | | |
|---|---|---|
| *A61K 8/55* | (2006.01) | |
| *A61K 8/49* | (2006.01) | |
| *A61Q 19/00* | (2006.01) | |
| *A61Q 17/00* | (2006.01) | |

(52) U.S. Cl.
CPC .............. *A61K 8/4913* (2013.01); *A61K 8/55* (2013.01); *A61Q 17/005* (2013.01); *A61Q 19/00* (2013.01); *A61Q 19/007* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 4,837,026 A | | 6/1989 | Rajakhyaksha |
| 5,334,713 A | * | 8/1994 | Hattori .................. C07J 43/003 540/113 |
| 6,296,859 B1 | | 10/2001 | Stoltz |
| 6,692,754 B1 | | 2/2004 | Makimoto et al. |
| 2002/0009472 A1 | | 1/2002 | Takekoshi et al. |
| 2008/0200534 A1 | | 8/2008 | Roso et al. |
| 2010/0055062 A1 | | 3/2010 | Arditty |
| 2015/0010489 A1 | | 1/2015 | Sugimoto |

FOREIGN PATENT DOCUMENTS

| | | |
|---|---|---|
| EP | 1 681 049 A1 | 7/2006 |
| JP | 2002-506016 | 2/2002 |
| JP | 2002-80321 | 3/2002 |
| JP | 2005-289873 | 10/2005 |
| JP | 2006-199714 | 8/2006 |
| JP | 2009-512667 | 3/2009 |
| JP | 2010-510284 | 4/2010 |
| WO | WO 99/45899 A1 | 9/1999 |
| WO | WO 2006/120851 A1 | 11/2006 |

OTHER PUBLICATIONS

International Search Report issued Oct. 15, 2013 in PCT/JP2013/068257 (with English translation).
Nippon Keshohin Seibun Hyoji Meisho Jiten, 1st edition, 1st print, Yakuji Nippo Ltd., Apr. 27, 2001, p. 119 (With a partial English translation).
ed. Takeo Mitsui, "New Cosmetics", New Cosmetic Science (2nd edition), Nanzando Co., Ltd., pp. 152-156 (with an English translation).
ed. Tsutomu Nishihara/Hiroki Kourai, "Development and Prospect of Biocontrol Agents", High Technology Information, CMC Publishing CO., LTD., p. 217 (with an English translation).
Extended Search Report issue Jan. 15, 2016 in European Patent Application No. 13813878.9.
English translation of Office Action dated Jun. 28, 2016 issued in corresponding Chinese patent application No. 201380035391.4.

* cited by examiner

*Primary Examiner* — Samantha Shterengarts
(74) *Attorney, Agent, or Firm* — Oblon, McClelland, Maier & Neustadt, L.L.P

(57) ABSTRACT

Provided is a moisturizer having hygroscopicity and water retention ability, and also provided is a composition superior in antiseptic property and feeling on application, in addition to moisturizing property, and free of coloration and odorization.

A moisturizer containing acylproline represented by the formula (1)

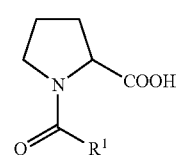

(1)

wherein an acyl group represented by $R^1$—CO— is an acyl group derived from a saturated or unsaturated fatty acid having 3-23 carbon atoms, or a salt thereof, and a composition containing (A) acylproline represented by the above formula (1) or a salt thereof and (B) bisphosphonate.

20 Claims, No Drawings

MOISTURIZER AND COSMETIC AGENT CONTAINING SAME

CROSS REFERENCES TO RELATED APPLICATIONS

This application is a continuation of International Patent Application No. PCT/JP2013/068257, filed on Jul. 3, 2013, and claims priority to Japanese Patent Application No. 2012-149015, filed on Jul. 3, 2012, all of which are incorporated herein by reference in their entireties.

BACKGROUND OF THE INVENTION

1. Field of the Invention

The present invention relates to a moisturizer containing a particular acylproline or a salt thereof, and a composition containing (A) the acylproline or a salt thereof and (B) bisphosphonate. Also, it relates to a cosmetic agent containing the above-mentioned moisturizer or composition.

2. Discussion of the Background

Skin's moisture level deeply relates to the maintenance of youthful skin. Therefore, various moisturizers are generally added to cosmetics to keep the skin's moisture level. Moisturizers are required to have hygroscopicity and retain water. Various moisturizers such as betaine, sodium lactate, pyrrolidonecarboxylic acid, glycerol, sorbitol and the like have been used heretofore (non-patent document 1). However, since none of them have both the hygroscopicity and water retention ability, they cannot necessarily provide a cosmetic agent that sufficiently maintains the skin's moisture level.

Moreover, 1,3-butyleneglycol is a material that potentiates a preservation effect while being effective as a moisturizer, and can also be an auxiliary for the preservative (non-patent document 2). Such multi-functional material is highly useful. However, the moisturizing effect and preservative effect of 1,3-butylene glycol are not sufficient, and a material having a higher effect is earnestly desired.

DOCUMENT LIST

Non-Patent Documents non-patent document 1:
New Cosmetic Science (2nd edition), ed. Takeo Mitsui, Nanzando, p 152-156
non-patent document 2:
Development and Prospect of Biocontrol Agents, ed. Tsutomu Nishihara/Hiroki Korai, CMC Publishing CO., LTD., p 217

SUMMARY OF THE INVENTION

Problems to be Solved by the Invention

The problem of the present invention is to provide a moisturizer having a function as a moisturizer, namely, having hygroscopicity and water retention ability, and also capable of potentiating a preservative effect, and a composition utilizing the moisturizer.

Means of Solving the Problems

The present inventors have conducted intensive studies in an attempt to solve the aforementioned problems and found that acylproline is a moisturizer that solves the above-mentioned problems, and further that a composition superior in the antiseptic property and feeling on application, in addition to the moisturizing property, and showing suppressed coloration and odorization can be provided by combining acylproline and bisphosphonate, and preferably also combining alcohol having 6-24 carbon atoms, which resulted in the completion of the present invention.

Accordingly, the present invention includes the following embodiments.

[1] A moisturizer comprising acylproline represented by the formula (1)

wherein an acyl group represented by $R^1$—CO— is an acyl group derived from a saturated or unsaturated fatty acid having 3-23 carbon atoms,
or a salt thereof.

[2] The moisturizer of the above-mentioned [1], wherein, in acylproline represented by the formula (1), the acyl group represented by $R^1$—CO— is an acyl group derived from a saturated or unsaturated fatty acid having 6-14 carbon atoms.

[3] The moisturizer of the above-mentioned [1] or [2], wherein acylproline represented by the formula (1) is decanoyl proline.

[4] The moisturizer of any of [1]-[3], wherein acylproline represented by the formula (1) or a salt thereof is a sodium salt of acylproline represented by the formula (1).

[5] A composition comprising
(A) acylproline represented by the formula (1)

wherein an acyl group represented by $R^1$—CO— is an acyl group derived from a saturated or unsaturated fatty acid having 3-23 carbon atoms, or a salt thereof, and
(B) bisphosphonate.

[6] The composition of the above-mentioned [5], wherein, in acylproline represented by the formula (1), the acyl group represented by $R^1$—CO— is an acyl group derived from a saturated or unsaturated fatty acid having 6-14 carbon atoms.

[7] The composition of the above-mentioned [5] or [6], wherein acylproline represented by the formula (1) is decanoyl proline.

[8] The composition of any of [5]-[7], wherein acylproline represented by the formula (1) or a salt thereof is a sodium salt of acylproline represented by the formula (1).

[9] The composition of any of [5]-[8], wherein (B) is etidronate.

[10] The composition of [9], wherein etidronate is added thereto in the form of etidronic acid.

[11] The composition of any one of [5]-[10], wherein the weight ratio of (A) to (B) is (A)/(B)=100000-3.

[12] The composition of [5]-[11], further comprising (C) alcohol having 6-24 carbon atoms.

[13] A cosmetic agent comprising the moisturizer of any of [1]-[4].

[14] A cosmetic agent comprising the composition of any of [5]-[12].

[15] The cosmetic agent of [13] or [14], which is an emulsion cosmetic agent.

[16] The cosmetic agent of [13]-[15], which is a washing agent.

[17] The cosmetic agent of [13]-[16], wherein is for the skin.

[18] Use of bisphosphonate (B) for suppressing decomposition of acylproline represented by the formula (1):

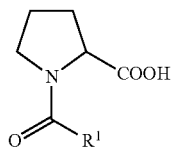

wherein an acyl group represented by $R^1$—CO— is an acyl group derived from a saturated or unsaturated fatty acid having 3-23 carbon atoms, or a salt thereof (A).

[19] Use of bisphosphonate (B) for preventing coloration and/or odorization of a composition comprising acylproline represented by the formula (1):

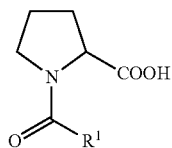

wherein an acyl group represented by $R^1$—CO— is an acyl group derived from a saturated or unsaturated fatty acid having 3-23 carbon atoms, or a salt thereof (A).

[20] A moisturizing method comprising applying acylproline represented by the formula (1):

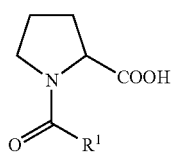

wherein an acyl group represented by $R^1$—CO— is an acyl group derived from a saturated or unsaturated fatty acid having 3-23 carbon atoms, or a salt thereof (A) to a subject.

[21] A method of suppressing decomposition of acylproline represented by the formula (1):

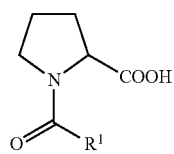

wherein an acyl group represented by $R^1$—CO— is an acyl group derived from a saturated or unsaturated fatty acid having 3-23 carbon atoms, or a salt thereof (A), comprising a step of achieving co-existence of bisphosphonate (B).

[22] A method of preventing coloration or odorization of a composition comprising acylproline represented by the formula (1):

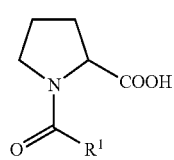

wherein an acyl group represented by $R^1$—CO— is an acyl group derived from a saturated or unsaturated fatty acid having 3-23 carbon atoms, or a salt thereof (A), comprising a step of achieving co-existence of bisphosphonate (B).

Effect of the Invention

Using the moisturizer of the present invention, a composition superior in moisturizing property can be provided. Furthermore, by combining acylproline or a salt thereof, and bisphosphonate, and further combining alcohol having 6-24 carbon atoms where necessary, a composition superior in the antiseptic property and feeling on application, in addition to the moisturizing property, and showing suppressed coloration and odorization can be provided.

Particularly, according to the present invention, a cosmetic agent superior in the moisturizing property and feeling on application, and showing suppressed coloration and odorization can be provided.

DETAILED DESCRIPTION OF THE PREFERRED EMBODIMENTS

[(A) Acylproline]

Acylproline in the present invention is represented by the formula (1):

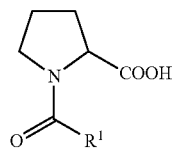

In the formula (1),

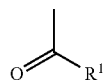

is also represented by $R^1$—CO— in the present specification.

The acyl group represented by $R^1$—CO— is an acyl group derived from a saturated or unsaturated fatty acid having 3-23 carbon atoms. Examples thereof include a propanoyl group, an isopropanoyl group, a butanoyl group, an isobutanoyl group, a sec-butanoyl group, a tert-butanoyl group, a pentanoyl group, an isopentanoyl group, a sec-pentanoyl group, a tert-pentanoyl group, a hexanoyl group, a heptanoyl group, an octanoyl group, a tert-octanoyl group, a 2-ethylhexanoyl group, a nonanoyl group, an isononanoyl group, a decanoyl group, an isodecanoyl group, an undecanoyl group, a lauroyl group, a myristoyl group, a palmitoyl group, a stearoyl group, a behenoyl group, an undecylenoyl group, an oleoyl group and the like.

The long chain acyl group represented by $R^1$—CO— may be, besides an acyl group derived from an acid having a single composition, an acyl group derived from naturally-occurring mixed fatty acid such as palm oil fatty acid, castor oil fatty acid, olive oil fatty acid, palm oil fatty acid and the like, or fatty acid (including branched fatty acid) obtained by synthesis. One kind of these may be used, or a mixture of two or more kinds selected from the above-mentioned group may be used.

The acyl group represented by $R^1$—CO— is preferably an acyl group derived from a saturated or unsaturated fatty acid having 4-18 carbon atoms, more preferably an acyl group derived from a saturated or unsaturated fatty acid having 6-14 carbon atoms, further preferably an acyl group derived from a saturated or unsaturated fatty acid having 10-12 carbon atoms, and furthermore preferably a decanoyl group.

An acyl group derived from a saturated fatty acid is more preferable than an acyl group derived from an unsaturated fatty acid.

Examples of the salt of acylproline represented by the formula (1) include alkali metal salts such as lithium salt, sodium salt, potassium salt and the like; alkaline earth metal salts such as calcium salt, magnesium salt and the like; ammonium salts such as alkanolamine salt and the like; basic organic salt and the like. Of these, from the aspect of solubility, alkali metal salt is preferable, sodium salt, potassium salt and ammonium salt are more preferable, sodium salt and potassium salt are further preferable, and sodium salt is particularly preferable.

Acylproline and a salt thereof in the present invention are known compounds.

The production method of acylproline in the present invention is not particularly limited, and it can be produced easily by combining known methods. To be specific, it can be prepared by the Schotten-Baumann method using proline and acid chloride. In this case, for example, acid chloride and a base such as sodium hydroxide and the like are simultaneously added dropwise. Proline may be an L form, a D form, or a mixture thereof, preferably an L form.

Since acylproline or a salt thereof in the present invention has both the hygroscopicity and water retention ability, it can be used as an active ingredient singly or as a good moisturizer in combination with other components. The moisturizer of the present invention can be added to, for example, cosmetic agents (including quasi-drugs) and the like.

When acylproline or a salt thereof in the present invention is used by addition to a composition such as a cosmetic agent and the like, the amount thereof is preferably 0.001 wt %-40 wt % relative to the total weight of the composition. The lower limit is more preferably 0.01 wt %, further preferably 0.05 wt %. From the aspect of texture of the composition, the upper limit is more preferably 35 wt %, more preferably 30 wt %, more preferably 20 wt %, more preferably 15 wt %, further preferably 10 wt %, still more preferably 5 wt %.

While superior moisturizing property can be achieved by using the above-mentioned component (A) alone, a composition superior in the antiseptic property and feeling on application, in addition to the moisturizing property, and showing no coloration and odorization by suppressing particular odor and color derived from component (A), can be provided by using (B) bisphosphonate in combination.

In the present invention, the moisturizer is for mammals inclusive of human.

[(B) Bisphosphonate]

Examples of bisphosphonate in the present invention include etidronate, clodronate, tiludronate and the like. Examples of the counter cation include alkali metal ions such as lithium, sodium, potassium and the like; alkaline earth metal ions such as calcium, magnesium and the like; ammonium ions such as alkanolamine and the like; and basic organic ions. Since a composition free of coloration and odorization can be provided, etidronate is desirable.

Etidronate may also be added to a composition in the form of etidronic acid.

The amount of bisphosphonate to be added to the composition of the present invention is preferably 0.00001 wt %-5 wt %. Since a composition free of coloration and odorization can be provided, the lower limit is more preferably 0.0001 wt %, further preferably 0.005 wt %. From the aspect of feeling on application of the composition, the upper limit is preferably 2 wt %, more preferably 1.5 wt %, further preferably 1 wt %, still more preferably 0.5 wt %.

For example, when it is added in the form of etidronic acid, it can be added in an amount based on the amount of bisphosphonate in the above-mentioned composition.

The weight ratio of (A) to (B) is preferably (A)/(B) (weight/weight)=100000-3 from the aspect of feeling on application, and since a composition free of coloration and odorization can be provided. The upper limit is more preferably 30000, more preferably 10000, more preferably 5000, more preferably 3000, more preferably 1500. From the aspect of antiseptic property, the lower limit is preferably 3, more preferably 10, more preferably 30, more preferably 100, more preferably 200.

A composition containing (A) acylproline or a salt thereof and (B) bisphosphonate can be prepared by simply mixing (A) acylproline or a salt thereof, and (B) bisphosphonate, or by mixing them in an appropriate solvent such as water and the like. The present invention also encompasses an embodiment wherein (B) is added to the composition in the form of bisphosphonic acid and mixing same with a suitable base to form bisphosphonate in the composition.

From the aspect of feeling on application, it is preferable to use (C) alcohol having 6-24 carbon atoms in combination with the above-mentioned (A) and (B).

[(C) Alcohol having 6-24 Carbon Atoms]

Examples of the alcohol having 6-24 carbon atoms of the present invention include lauryl alcohol, myristyl alcohol, cetyl alcohol, stearyl alcohol, behenyl alcohol, isostearyl alcohol, octyldodecanol and the like. Since the feeling on application is more superior, alcohol having 16-20 carbon atoms such as cetyl alcohol, stearyl alcohol, behenyl alcohol, isostearyl alcohol, octyldodecanol and the like are desirable, and cetyl alcohol and stearyl alcohol are more desirable.

The amount of (C) alcohol having 6-24 carbon atoms in the composition of the present invention is preferably 0.01 wt %-20 wt %. In view of the feeling on application of the composition, the lower limit is more preferably 0.1 wt %, further preferably 0.5 wt %. On the other hand, in view of the feeling on application of the composition, the upper limit is preferably 15 wt %, more preferably 10 wt %, further preferably 5 wt %.

The moisturizer and the composition of the present invention can be added to various cosmetic agents. The cosmetic agent of the present invention is not particularly limited as to the form, and can take any form such as liquid, emulsion, paste, gel, solid, powder and the like. Among these, an emulsion cosmetic agent is preferable.

Examples of the cosmetic agent of the present invention include cosmetic agents for skin such as facial wash, skin lotion, skin milk, cream, gel, serum, facial mask, mask, soap, body shampoo, face powder, foundation, lip rouge, blush, eyeliner, mascara, eye shadow, eyebrow pencil and the like, and cosmetic agents for hair such as shampoo, rinse, conditioner, hair styling products, hair treatment and the like. While any cosmetic agent can be produced, a washing agent such as facial wash, shampoo, body shampoo and the like is preferable. A cosmetic agent for the skin requiring moisturization is more preferable.

The cosmetic agents may contain components that can be normally added to cosmetic agents as long as the effect of the present invention is not inhibited. Specific examples include oil solution, chelating agent, surfactant, powder, amino acid, polyamino acid and a salt thereof, sugar alcohol and an alkylene oxide adduct thereof, lower alcohol, animal and plant extracts, nucleic acid, vitamin, enzyme, anti-inflammatory agent, antimicrobial agent, preservative, antioxidant, UV absorber, adiaphoretic, pigment, dye, oxidation dye, organic and inorganic powders, pH adjuster, pearly sheen agent, wetting agent and the like. These are some examples, and components other than these may of course be added.

Examples of the oil solution include fatty acids such as ostearic acid, undecylenoic acid, oleic acid and the like; esters such as myristyl myristate, hexyl laurate, decyl oleate, isopropyl myristate, hexyldecyl dimethyloctanoate, glycerol monostearate, diethyl phthalate, ethylene glycol monostearate, cetyl octanoate, octyl oxystearate, benzoic acid alkyl ester and the like; hydrocarbons such as liquid paraffin, polyisobutene, petrolatum, squalane and the like; wax such as lanolin, reduced lanolin, Carnauba wax and the like; fats and oils such as silicone oil, mink oil, cacao oil, palm oil, palm kernel oil, camellia oil, sesame oil, castor oil, olive oil, jojoba oil and the like; and ethylene.α-olefin.cooligomer and the like.

Particularly, examples of the silicone oil include silicone oil selected from ether-modified silicone such as methylpolysiloxane, highly polymerized methylpolysiloxane, polyoxyethylene.methylpolysiloxane copolymer, polyoxypropylene.methylpolysiloxane copolymer, poly(oxyethylene, oxypropylene) methylpolysiloxane copolymer and the like, stearoxy methylpolysiloxane, stearoxy trimethylsilane, methylhydrogenpolysiloxane, cyclic silicones such as decamethylcyclopentasiloxane, octamethylcyclotetrasiloxane, tetrahydrotetramethylcyclotetrasiloxane, methylcyclopolysiloxane, dodecamethylcyclohexasiloxane and the like; methylphenylpolysiloxane, trimethylsiloxysilicic acid, amino-modified silicones such as aminoethylaminopropylsiloxane.dimethylsiloxane copolymer and the like, silanol-modified polysiloxane, alkoxy-modified polysiloxane, fatty acid-modified polysiloxane, fluorine-modified polysiloxane, epoxy-modified polysiloxane, alkoxy-modified polysiloxane perfluoropolyether, polyvinyl acetatedimethylpolysiloxane, and mixtures thereof.

While the chelating agent is not particularly limited, preferable examples thereof include chelating agents selected from triethylenetetramine, 2-thenoyltrifluoroacetone, thioglycolic acid, tartaric acid, succinic acid, 8-quinolinol, pyridine-2,6-dicarboxylic acid, pyridine, 1,10-phenanthroline, lactic acid, 8-hydroxyquinoline-5-sulfonic acid, glycine, 2,2'-pyridylethylenediamine, aurintricarboxylic acid, xylenol orange, 5-sulfosalicylic acid, salicylic acid, pyrocatechol-3,5-disulfonate, 4,5-dihydroxybenzene-1,3-disulfonic acid, 1,2-diaminocyclohexane-N,N,N',N'-tetraacetic acid, citric acid, oxalate, nitrilotriacetic acid, ethylenediamine-N,N,N',N'-tetraacetic acid (EDTA), acetylacetone and a salt thereof, a mixture thereof and the like.

Examples of the surfactant include anionic surfactant such as N-long chain acylamino acid salts (N-long chain acyl acidic amino acid salt, N-long chain acyl neutral amino acid salt and the like), N-long chain fatty acid acyl-N-methyltaurine salt, alkylsulfate and an alkylene oxide adduct thereof, fatty acid amide ethersulfate, metal salt and weak base salt of fatty acid, sulfosuccinic acid-based surfactant, alkylphosphate and an alkylene oxide adduct thereof, alkylethercarboxylic acid and the like; non-ionic surfactant such as ether type surfactant such as glycerolether and an alkylene oxide adduct thereof and the like, ester type surfactant such as glycerolester and an alkylene oxide adduct thereof and the like, etherester type surfactant such as sorbitan ester and an alkylene oxide adduct thereof and the like, ester type surfactant such as polyoxyalkylene fatty acid ester, glycerolester, fatty acid polyglycerolester, sorbitan ester, sucrose ester of fatty acid and the like, alkylglucosides, hydrogenated castor oil pyroglutamic acid diester and an ethyleneoxide adduct thereof, and nitrogen-containing type surfactant such as fatty acid alkanolamide and the like, cationic surfactant such as aliphatic amine salt (alkylammonium chloride, dialkylammonium chloride and the like), quaternary ammonium salt thereof, aromatic quaternary ammonium salt (benzalkonium salt and the like), fatty acid acylarginine ester and the like; and amphoteric surfactant such as betaine type surfactant (carboxybetaine and the like), aminocarboxylic acid type surfactant, imidazoline type surfactant and the like and the like.

Examples of the powder include resin powders such as nylon bead, silicone bead and the like, nylon powder, metal fatty acid soap, yellow iron oxide, red iron oxide, black iron oxide, chrome oxide, cobalt oxide, carbon black, ultramarine blue, iron blue, zinc oxide, titanium oxide, zirconium oxide, silicon oxide, aluminum oxide, cerium oxide, micatitanium, boron nitride, barium sulfate, calcium carbonate, magnesium carbonate, aluminum silicate, magnesium silicate, silicon carbide, dye, lake, sericite, mica, talc, kaolin, plate barium sulfate, butterfly barium sulfate, titanium oxide fine particles, zinc oxide fine particles, iron oxide fine particles, acylamino acids such as acyllysine, acylglutamic acid, acylarginine, acylglycine and the like and the like, which may be further subjected to a surface treatment such as silicone treatment, fluorine compound treatment, silane coupling agent treatment, silane-treated organic titanate treatment, acylation lysine treatment, fatty acid treatment, metal soap treatment, oil solution treatment, amino acid treatment and the like.

Examples of amino acid include glycine, alanine, serine, threonine, arginine, glutamic acid, aspartic acid, isoleucine, leucine, valine and the like.

Examples of polyamino acid and a salt thereof include polyglutamic acid, polyaspartic acid and the like.

Examples of sugar alcohol and an alkylene oxide adduct thereof include mannitol, sorbitol and the like.

Examples of lower alcohol include ethanol, propanol and the like.

Use of bisphosphonate (B) to suppress decomposition of acylproline represented by the formula (1) or a salt thereof (A) is also one embodiment of the present invention. Each definition is as described above.

Use of bisphosphonate (B) to prevent coloration and/or odorization of a composition containing acylproline represented by the formula (1) or a salt thereof (A) is also another embodiment of the present invention. Each definition is as described above.

A moisturizing method including applying acylproline represented by the formula (1) or a salt thereof (A) to a subject is also another embodiment of the present invention. Each definition is as described above.

As used herein, the application means to apply acylproline or a salt thereof singly, or in the form of the above-mentioned composition or cosmetic agent, to a subject in need thereof, by topically applying an effective amount of acylproline and the like to the skin and the like. Examples thereof include application in the form of cream, gel and the like onto the skin, spraying a liquid preparation, and the like. In general, the "effective amount" is, for example, an amount of the aforementioned composition and the like to be applied according to the symptoms, though it varies depending on the age, sex, symptom of the subject, application site, dosage form of the composition and the like.

A method of suppressing decomposition of acylproline represented by the formula (1) or a salt thereof (A), which includes a step of achieving co-existence of bisphosphonate (B), is also another embodiment of the present invention. According to the method of the present invention, it is possible to suppress decomposition of (A) and stabilize (A) by simple co-existence of (B), and a stable composition or cosmetic agent can be provided. Each definition is as described above.

A method of preventing coloration or odorization of a composition containing acylproline represented by the formula (1) or a salt thereof (A), which includes a step of achieving co-existence of bisphosphonate (B), is also another embodiment of the present invention. According to the method of the present invention, it is possible to prevent particular coloration and odorization of compositions containing (A), and a composition most suitable for a cosmetic agent and the like can be prepared. Each definition is as described above.

The present invention is explained in more detail in the following by referring to Examples, which are not to be construed as limitative.

EXAMPLES

Synthetic Example 1

Synthesis of Decanoyl Proline

Proline (manufactured by Ajinomoto Co., Inc., 34.54 g) was dissolved in water (100 g), and decanoyl chloride (manufactured by Tokyo Chemical Industry Co., Ltd., 52.01 g) and 25% aqueous sodium hydroxide solution were added while adjusting pH to 12. 75% Sulfuric acid was added to neutralize the mixture. The aqueous layer was removed, water and ethyl acetate were further added, and the aqueous layer was removed. Ethyl acetate was evaporated under reduced pressure to give decanoyl proline (68.12 g).

Synthetic Example 2

Preparation of Decanoyl Proline Sodium Salt

Decanoyl proline obtained in Synthetic Example 1 was suspended in a suitable amount of water, and the mixture was neutralized with sodium hydroxide to pH 7 and dried by concentration to give a decanoyl proline sodium salt.

Synthetic Example 3

Synthesis of Lauroylproline

Using proline and lauroyl chloride (manufactured by Tokyo Chemical Industry Co., Ltd.) and by a method similar to that in Synthetic Example 1, lauroylproline was synthesized.

Synthetic Example 4

Synthesis of Lauroylproline Sodium Salt

Using lauroylproline obtained in Synthetic Example 3 and by a method similar to that in Synthetic Example 2, a lauroylproline sodium salt was synthesized.

<Evaluation of Moisturizer>

To study the hygroscopicity and water retention ability of moisturizers, the following experiment was performed.

Decanoyl proline sodium obtained in Synthetic Example 2, betaine ("aminocoat" manufactured by Asahi Kasei Corporation), sodium lactate (manufactured by Wako), sodium pyrrolidonecarboxylate ("AJIDEW" NL-50 manufactured by Ajinomoto Co., Inc.), glycerol ("concentrated glycerin" manufactured by Kao Corporation), and sorbitol (manufactured by Kao Corporation) were each dried under vacuum. The moisture level of the samples was measured by Karl Fischer moisture meter, the amount of water was determined, and the weight other than the moisture level was calculated ([1]). Thereafter, the samples were allowed to absorb moisture under the conditions of 65% RH, 25° C. for 14 days, and the weight was measured ([2]). Thereafter, the samples were dried under the conditions of 35% RH, 25° C. for 14 days, and the weight was measured ([3]).

[Hygroscopicity]

$A(\%)=([2]-[1])/[1]\times 100$ was calculated and the samples were evaluated according to the following criteria.

⊙: value of A is not less than 15%
○: value of A is not less than 12% and less than 15%
Δ: value of A is not less than 10% and less than 12%
×: value of A is less than 10%

[Water Retention Ability]

$R(\%)=[3]/[2]\times 100$ was calculated and the samples were evaluated according to the following criteria.

⊙: value of R is not less than 80%
○: value of R is not less than 60% and less than 80%
Δ: value of R is not less than 40% and less than 60%
×: value of R is less than 40%

TABLE 1

| | | evaluation | |
|---|---|---|---|
| | | hygro-scopicity | water retention ability |
| Example 1 | compound of Synthetic Example 2 (decanoyl proline Na) | ⊙ | ⊙ |
| Comparative Example 1 | betaine | ⊙ | Δ |
| Comparative Example 2 | sodium lactate | ⊙ | × |
| Comparative Example 3 | sodium pyrrolidonecarboxylate | ⊙ | × |
| Comparative Example 4 | glycerol | ⊙ | × |
| Comparative Example 5 | sorbitol | × | × |

As shown in Table 1, it has been clarified that the moisturizer of Example 1 is superior in the water retention ability as compared to other moisturizers, and can be used as a moisturizer having both the hygroscopicity and water retention ability.

<Evaluation of Composition>

The compositions described in Table 2 were evaluated for the coloration/coloration suppressive effect, odorization/odorization suppressive effect, antibacterial property, moisturizing property, stability against decomposition, and feeling on application. The results are shown below.

[Coloration]

The compositions described in Table 2 were prepared, and each composition was preserved under acceleration test conditions of 70° C. for 14 days. Using a 10 mm cell, the transmittance at a wavelength of 430 nm was measured. Coloration was evaluated according to the following evaluation criteria.

⊙: transmittance is not less than 93%
○: transmittance is not less than 85% and less than 93%
Δ: transmittance is not less than 75% and less than 85%
×: transmittance is less than 75%

[Coloration Suppressive Effect]

The compositions described in Table 2 and compositions, which are the compositions described in Table 2 without component B (or component B'), were prepared, and each composition was preserved under acceleration test conditions of 70° C. for 14 days. Using a 10 mm cell, the transmittance at a wavelength of 430 nm was measured, and the coloration suppressive effect of component B was evaluated according to the following evaluation criteria.

⊙: transmittance is improved by not less than 40% compared to composition free of Component B (or component B')
○: transmittance is improved by not less than 25% and less than 40% compared to composition free of Component B (or component B')
Δ: transmittance is improved by not less than 10% and less than 25% compared to composition free of Component B (or component B')
×: transmittance is improved only by less than 10% or is not improved at all compared to composition free of Component B (or component B')

[Odorization]

The compositions described in Table 2 were prepared, and each composition was preserved under acceleration test conditions of 70° C. for 14 days. Odorization was evaluated by five professional panelists according to the following evaluation criteria.

⊙: completely no odor
○: scarce odor
Δ: slight odor
×: considerable odor

[Odorization Suppressive Effect]

The compositions described in Table 2 and compositions, which are the compositions described in Table 2 without component B (or component B'), were prepared, and each composition was preserved under acceleration test conditions of 70° C. for 14 days. Odorization suppressive effect was evaluated by five professional panelists according to the following evaluation criteria.

5: completely no odor as compared to composition free of Component B (or component B')
4: slight odor as compared to composition free of Component B (or component B')
3: some odor as compared to composition free of Component B (or component B')
2: considerable odor as compared to composition free of Component B (or component B')
1: odor as compared to composition free of Component B (or component B')

The average evaluation points of the five panelists of not less than 4.0 and less than 5.0 was marked with ⊙, not less than 3.0 and less than 4.0 was marked with ○, not less than 2.0 and less than 3.0 was marked with Δ, and less than 2.0 was marked with ×.

[Antiseptic Property]

The compositions described in Table 2 were prepared and each composition was subjected to a preservative-effectiveness test against *Aspergillus niger*. The evaluation criteria are shown below.

⊙: fungi died 14 days later
○: fungi died 28 days later
×: fungi did not die even 28 days later

[Moisturizing Property]

Creams containing the components of Table 2 were prepared, and the moist feeling after application onto the skin was evaluated by five professional panelists according to the following evaluation criteria.

To prepare the cream, squalane (8.8 wt %), jojoba oil (5.0 wt %) and glyceryl stearate (2.9 wt %) were dissolved in advance by heating at 85° C. Separately, sucrose palmitate (0.4 wt %), sodium stearoyl glutamate (0.1 wt %), citrate buffer (suitable amount added until pH 6.0), the composition described in Table 2 (0.5 wt %), and water (balance) were each dissolved by heating at 85° C. They were gradually mixed and cooled to room temperature to give the cream. The wt % in the above-mentioned parentheses shows a concentration relative to the whole weight of the cream.

4 points: high moist feeling
3 points: considerable moist feeling
2 points: moist feeling
1 point: not much moist feeling
0 point: no moist feeling at all The average points of the professional panelists of not less than 3.5 was marked with ⊙, not less than 2.5 and less than 3.5 was marked with ○, not less than 1.5 and less than 2.5 was marked with Δ, and less than 1.5 was marked with ×.

TABLE 2

|  | Ex. 2 | Ex. 3 | Ref. Ex. 1 | Ref. Ex. 2 | Com. Ex. 6 | Com. Ex. 7 | Com. Ex. 8 | Com. Ex. 9 |
|---|---|---|---|---|---|---|---|---|
| A compound of Synthetic Example 2 (decanoyl proline Na) | 30.0 |  | 15.0 | 27.0 |  |  |  |  |
| compound of Synthetic Example 4 (lauroylproline Na) |  | 30.0 |  |  |  |  |  |  |
| A' acetylproline |  |  |  |  | 30.0 |  |  |  |
| acetyl glutamic acid |  |  |  |  |  | 30.0 |  |  |
| sodium lauroyl glutamate |  |  |  |  |  |  | 30.0 |  |
| sodium lauroyl glycinate |  |  |  |  |  |  |  | 30.0 |
| B etidronate | 0.025 | 0.1 |  |  | 0.1 | 0.1 | 0.1 | 0.1 |
| B' EDTA |  |  |  | 0.1 |  |  |  |  |
| water | balance | balance | balance | balance | balance | balance | balance | balance |
| coloration | ⊙ | ○ | X | X | ○ | ○ | X | ⊙ |
| coloration suppressive effect | ○ | ○ | — | X | X | X | X | X |
| odorization | ⊙ | ○ | X | X | ○ | ○ | ○ | ○ |
| odorization suppressive effect | ⊙ | ⊙ | — | X | X | X | X | X |
| antiseptic property | ⊙ | ⊙ | ○ | ⊙ | X | X | X | X |
| moisturizing property | ⊙ | ⊙ | ⊙ | ⊙ | Δ | X | X | X |

From the results of Table 2, it has been clarified that the composition containing component A and component B of the present invention is a composition superior in the antiseptic property in addition to the moisturizing property and free of coloration and odorization. As is clear from Reference Examples 1 and 2, the composition containing decanoyl proline Na was superior in the moisturizing property.

Skin lotions shown in the following Table were prepared.

TABLE 3

|  | Example 4 | Example 5 | Example 6 | Example 7 |
|---|---|---|---|---|
| sodium hyaluronate | 0.10 | 0.10 | 0.10 | 0.10 |
| water | 80.80 | 76.80 | 61.80 | 81.30 |
| sorbitol | 5.00 | 5.00 | 5.00 | 5.00 |
| sodium pyrrolidonecarboxylate | 3.00 | 3.00 | 3.00 | 3.00 |
| compound of Synthetic Example 2 (decanoyl proline Na) | 1.00 | 5.00 | 20.00 | 0.50 |
| glycerol | 5.00 | 5.00 | 5.00 | 5.00 |
| ethanol | 5.00 | 5.00 | 5.00 | 5.00 |
| citric acid | 0.10 | 0.10 | 0.10 | 0.10 |
| etidronate | 0.01 | 0.02 | 0.001 | 0.05 |

The skin lotions of Table 3 were, as in Examples 2 and 3, compositions superior in the antiseptic property in addition to the moisturizing property, and free of coloration and odorization. Particularly, the skin lotions of Example 4 and Example 5 were furthermore superior.

[Stability Against Decomposition]

Solutions of the compound of Synthetic Example 2 (decanoyl proline Na, 30.0 wt %) in water with or without addition of etidronate to 0.1 wt % were prepared, and they were subjected to an acceleration test at 70° C. for 22 days. The decomposition rate of the compound of Synthetic Example 2 in each composition was measured using HPLC (20A manufactured by Shimadzu Corporation).

When etidronate was added, the decomposition rate of decanoyl proline Na was 0.8%. When etidronate was not added, the decomposition rate of decanoyl proline Na was 2.4%. Therefrom it has been clarified that the addition of etidronate prevents decomposition of acylproline.

[Feeling on Application]

Creams having the compositions shown in the following Table were prepared, and the thickness on application to the skin was evaluated by five professional panelists according to the pair test.

As a result, Example 8 received higher evaluation of the feeling on application than Reference Example 3.

TABLE 4

| (mass %) | Example 8 | Reference Example 3 |
|---|---|---|
| squalane | 8.8 | 8.8 |
| jojoba oil | 5 | 5 |
| glyceryl stearate | 2.9 | 2.9 |
| stearylalcohol | 3.8 |  |
| sucrose palmitate | 0.4 | 0.4 |
| sodium stearoyl glutamate | 0.1 | 0.1 |
| compound of Synthetic Example 2 (sodium decanoyl prolinate) | 0.5 | 0.5 |
| etidronate | 0.0025 |  |
| citrate buffer | q.s. | q.s. |
| water | balance | balance |
|  | 100 | 100 |

From the above-mentioned test, it has been clarified that the addition of etidronate and alcohol having 6-24 carbon atoms improves the feeling on application.

Formulation Example 1

Preparation of Solubilized Skin Lotion

A skin lotion having the following formulation was produced.

|  | (mass %) |
|---|---|
| compound of Synthetic Example 2 (decanoyl proline Na) | 0.50 |
| etidronate | 0.0001 |
| phytosteryl/octyldodecyl lauroyl glutamate | 0.35 |
| cetyl octanoate | 0.15 |
| PPG-8 ceteth-20 | 0.50 |
| PPG-6 decyltetradeceth-30 | 0.50 |
| glycerol | 1.25 |
| water | 5.00 |
| DPG | 2.00 |
| BG | 3.00 |
| citrate buffer | q.s. |
| water | balance |
|  | 100.00 |

Formulation Example 2

Preparation of Cleansing Foam

A cleansing foam having the following formulation was produced.

| | (mass %) |
|---|---|
| cocoylglycine Na (30%) | 33.0 |
| Lauramide propylbetaine (30%) | 13.0 |
| compound of Synthetic Example 2 (decanoyl proline Na) | 2.0 |
| glyceryl caprylate | 1.1 |
| glycerol | 25.0 |
| water | 20.4 |
| jojoba oil | 3.0 |
| hydroxypropylstarch phosphoric acid | 2.5 |
| aqueous citric acid solution (20%) | q.s. |
| etidronate | 0.01 |
| balance water | balance |
| | 100.0 |

Formulation Example 3

W/O Foundation Cream

A foundation cream having the following formulation was produced.

| | | (mass %) |
|---|---|---|
| A | cyclomethicone | 20.00 |
| | dimethicone | 4.90 |
| | (dimethicone/vinyldimethicone)crosspolymer | 1.00 |
| | cetyl octanoate | 6.00 |
| | tri(capril/capric acid)glyceryl | 4.00 |
| | PEG-9 polydimethylsiloxyethyl dimethicone | 2.50 |
| | Quaternium-18 hectorite | 1.50 |
| | distearyldimonium chloride | 0.10 |
| | nylon powder | 1.00 |
| | pigment | 14.00 |
| B | EDTA-2Na | 0.05 |
| | glutamic acid Na | 1.00 |
| | sodium chloride | 0.50 |
| | sorbic acid K | 0.20 |
| | BG | 7.00 |
| | glycerol | 5.00 |
| | water | balance |
| | compound of Synthetic Example 2 (decanoyl proline Na) | 0.20 |
| | etidronate | 0.01 |
| C | flavor | q.s. |
| | total | 100 |

Preparation method: Component A and component B were respectively heated to 70° C., and component B was gradually added to stirring component A to emulsify the mixture. After cooling to 50° C., component C was added, and the mixture was further cooled to room temperature.

Formulation Example 4

Base Cream

A base cream having the following formulation was produced.

| | | (mass %) |
|---|---|---|
| A | cyclomethicone | 20.00 |
| | isononyl isononanoate | 4.00 |
| | phytosteryl/octyldodecyl lauroyl glutamate | 3.00 |
| | octyl methoxycinnamate | 3.00 |
| | diisostearic acid polyglyceryl-2 | 2.00 |
| | PEG-10 dimethicone | 2.00 |
| | dimethicone | 2.00 |
| | dextrin palmitate | 0.20 |
| | tocopherol acetate | 0.10 |
| | ethylhexylglycerol | 0.10 |
| | Quaternium-18 bentonite | 1.30 |
| | pigment | 10.00 |
| B | pentyleneglycol | 0.20 |
| | BG | 5.00 |
| | PCA-Na | 2.00 |
| | glycerol | 5.00 |
| | water | balance |
| | compound of Synthetic Example 2 (decanoyl proline Na) | 0.20 |
| | etidronate | 0.01 |
| C | flavor | q.s. |
| | total | 100 |

Preparation method: Component A and component B were respectively heated to 60° C., and component B was gradually added to stirring component A. The mixture was cooled, component C was added at 50° C., and the mixture was cooled to 30° C.

Formulation Example 5

Emollient Skin Lotion

An emollient cream having the following formulation was produced.

| | | (mass %) |
|---|---|---|
| A | phytosteryl/octyldodecyl lauroyl glutamate | 0.10 |
| | tocopherol acetate | 0.05 |
| | phenyl trimethicone | 0.70 |
| | isostearic acid PEG-15 glyceryl | 1.00 |
| | hydrogenated lecithin | 0.05 |
| | PEG-20 hydrogenated castor oil | 0.05 |
| | benzyl alcohol | 0.05 |
| | phenethyl alcohol | 0.10 |
| B | BG | 5.00 |
| | Cocoylalanine TEA (30% aqueous solution) | 0.10 |
| | chondroitin sulfate Na | 0.05 |
| | trehalose | 1.00 |
| | glycerol | 2.00 |
| | water | balance |
| | compound of Synthetic Example 2 (decanoyl proline Na) | 0.20 |
| | etidronate | 0.01 |
| C | flavor | q.s. |
| | PEG-20 hydrogenated castor oil | 0.05 |
| | ethanol | 4.00 |
| | water | 2.00 |
| | total | 100 |

Preparation method: Component A and component B were respectively heated to 70° C., and component A was gradually added to stirring component B. Component C was added at 40° C., and the mixture was cooled to give the cream.

Formulation Example 6

W/O Emollient Cream

A W/O emollient cream having the following formulation was produced.

|   |   | (mass %) |
|---|---|---|
| A | cyclomethicone | 10.00 |
|   | dimethicone | 7.00 |
|   | squalane | 2.00 |
|   | cetyl octanoate | 4.00 |
|   | (dimethicone/vinyldimethicone)crosspolymer | 1.00 |
|   | PEG-10 dimethicone | 2.50 |
|   | Quaternium-18 hectorite | 2.00 |
|   | phenoxyethanol | 0.45 |
|   | acrylic acid/acrylic acid alkyl (C10-30) | 0.05 |
| B | Ascorbyl-2-phosphate magnesium | 0.40 |
|   | serine | 0.20 |
|   | glycine | 0.20 |
|   | PEG-75 | 1.00 |
|   | methylparaben | 0.20 |
|   | salicylic acid Na | 0.01 |
|   | BG | 5.00 |
|   | glycerol | 15.00 |
|   | water | balance |
|   | compound of Synthetic Example 2 (decanoyl proline Na) | 0.20 |
|   | etidronate | 0.01 |
|   | total | 100 |

Preparation method: Component A and component B were respectively heated to 60° C., and component A was gradually added to stirring component B, and the mixture was cooled to give the cream.

Formulation Example 7

W/O Emollient Milk

A W/O emollient milk having the following formulation was produced.

|   |   | (mass %) |
|---|---|---|
| A | cyclomethicone | 9.00 |
|   | dimethicone | 4.00 |
|   | phytosteryl/octyldodecyl lauroyl glutamate | 2.00 |
|   | PEG-9 polydimethylsiloxyethyl dimethicone | 1.50 |
|   | squalane | 1.00 |
|   | (dimethicone/vinyldimethicone)crosspolymer | 0.30 |
|   | quaternium 18 bentonite | 0.20 |
|   | tocopherol acetate | 0.10 |
|   | (vinyldimethicone/methicone silsesquioxane)crosspolymer | 0.10 |
|   | flavor | q.s. |
| B | glycerol | 5.00 |
|   | DPG | 3.00 |
|   | BG | 2.00 |
|   | methylparaben | 0.20 |
|   | PEG-75 | 1.00 |
|   | PCA-Na (50% aqueous solution) | 1.00 |

-continued

|   |   | (mass %) |
|---|---|---|
|   | NaCl | 0.30 |
|   | ethanol | 0.50 |
|   | water | balance |
|   | compound of Synthetic Example 2 (decanoyl proline Na) | 0.20 |
|   | etidronate | 0.01 |
|   | total | 100 |

Preparation method: Component A and component B were respectively dissolved at room temperature, and component B was gradually added to stirring component A to give the milk.

Formulation Example 8

O/W Moisture Cream

An O/W moisture cream having the following formulation was produced.

|   |   | (mass %) |
|---|---|---|
| A | squalane | 4.00 |
|   | cetyl octanoate | 10.00 |
|   | phytosteryl/octyldodecyl lauroyl glutamate | 5.00 |
|   | (dimethicone/vinyldimethicone)crosspolymer | 2.00 |
|   | dimethicone | 5.00 |
|   | behenyl alcohol | 0.80 |
|   | stearylalcohol | 2.00 |
|   | glyceryl stearate (SE) | 3.00 |
|   | stearic acid polyglycerol-6 | 1.50 |
|   | hydrogenated lecithin | 1.00 |
|   | acetic acid tocopherol | 0.10 |
|   | bisabolol | 0.10 |
|   | chlorphenesin | 0.05 |
|   | caprylyl glycol | 0.10 |
| B | sodium stearoyl glutamate | 0.40 |
|   | PEG-75 | 1.00 |
|   | trehalose | 2.00 |
|   | BG | 5.00 |
|   | glycerol | 13.00 |
|   | xanthan gum (1% aqueous solution) | 10.00 |
|   | water | balance |
|   | compound of Synthetic Example 2 (decanoyl proline Na) | 0.20 |
|   | etidronate | 0.01 |
|   | total | 100 |

Preparation method: Component A and component B were respectively heated to 70° C., and component B was gradually added to stirring component A. Thereafter, the mixture was cooled to give the cream.

Formulation Example 9

O/W Moisture Skin Milk

An O/W moisture skin milk having the following formulation was produced.

|   |   | (mass %) |
|---|---|---|
| A | phytosteryl/octyldodecyl lauroyl glutamate | 6.00 |
|   | dimethicone | 1.50 |

-continued

| | | (mass %) |
|---|---|---|
| | glyceryl stearate | 0.50 |
| | distearic acid polyglycerol-2 | 1.50 |
| | capryloyl glycine | 0.05 |
| B | sodium dehydroacetate | 0.10 |
| | hydrogenated lecithin | 0.50 |
| | maltitol | 5.00 |
| | BG | 10.00 |
| | glycerol | 5.00 |
| | carboxyvinyl polymer (1% aqueous solution) | 10.00 |
| | water | balance |
| | compound of Synthetic Example 2 (decanoyl proline Na) | 0.20 |
| | etidronate | 0.01 |
| C | arginine | 0.10 |
| | water | 2.00 |
| | total | 100 |

Preparation method: Component A, component B and component C were respectively heated to 70° C., component A and component C were gradually added to stirring component B, and the mixture was cooled to give the milk.

Formulation Example 10

Massage Cream

A massage cream having the following formulation was produced.

| | | (mass %) |
|---|---|---|
| A | liquid paraffin | 30.00 |
| | solid paraffin | 5.00 |
| | beeswax | 2.00 |
| | cetyl octanoate | 19.40 |
| | phytosteryl/octyldodecyl lauroyl glutamate | 5.00 |
| | behenyl alcohol | 2.00 |
| | glyceryl stearate | 3.00 |
| | sorbitan stearate | 1.50 |
| | stearic acid PEG-30 | 2.00 |
| | butylparaben | 0.10 |
| B | methylparaben | 0.20 |
| | PEG-30 | 1.00 |
| | sodium stearoyl glutamate | 0.50 |
| | BG | 5.00 |
| | xanthan gum (1% aqueous solution) | 10.00 |
| | water | balance |
| | compound of Synthetic Example 2 (decanoyl proline Na) | 0.20 |
| | etidronate | 0.01 |
| | total | 100 |

Preparation method: Component A and component B were respectively heated to 70° C., component A was gradually added to stirring component B, and the mixture was cooled to give the cream.

Formulation Example 11

UV Cream

A UV cream having the following formulation was produced.

| | | (mass %) |
|---|---|---|
| A | cyclomethicone | 20.00 |
| | (dimethicone/(PEG-10/15))crosspolymer | 1.50 |
| | (dimethicone/vinyldimethicone)crosspolymer | 1.00 |
| | dimethicone | 7.50 |
| | phytosteryl/octyldodecyl lauroyl glutamate | 3.00 |
| | isononyl isononanoate | 5.00 |
| | PEG-9 polydimethylsiloxyethyl dimethicone | 2.00 |
| | titanium oxide | 10.00 |
| | zinc oxide | 10.00 |
| | dimethoxybenzylidenedioxoimidazolidine-propionate octyl | 0.30 |
| | butylparaben | 0.10 |
| B | methylparaben | 0.20 |
| | DPG | 5.00 |
| | sodium citrate | 0.30 |
| | NaCl | 1.00 |
| | water | balance |
| | compound of Synthetic Example 2 (decanoyl proline Na) | 0.20 |
| | etidronate | 0.01 |
| | total | 100 |

Preparation method: Component A and component B were respectively heated to 70° C., component B was gradually added to stirring component A, and the mixture was cooled to give the cream.

Formulation Example 12

UV Toner

A UV toner having the following formulation was produced.

| | | (mass %) |
|---|---|---|
| A | cyclomethicone | 30.90 |
| | phytosteryl/octyldodecyl lauroyl glutamate | 5.00 |
| | Quaternium-18 bentonite | 1.00 |
| | dimethicone | 5.00 |
| | octyl methoxycinnamate | 5.00 |
| | PEG-10 dimethicone | 1.00 |
| | polyglyceryl diisostearate-2 | 1.00 |
| | phenoxyethanol | 0.10 |
| | titanium oxide | 5.00 |
| | zinc oxide | 6.00 |
| B | BG | 3.00 |
| | water | balance |
| C | methylparaben | 0.10 |
| | flavor | q.s. |
| | ethyl alcohol | 1.00 |
| | compound of Synthetic Example 2 (decanoyl proline Na) | 0.20 |
| | etidronate | 0.01 |
| | total | 100 |

Preparation method: Component A and component B were dissolved by stirring at room temperature, and component B and component C were gradually added to stirring component A.

Formulation Example 13

Lip Rouge

A lip rouge having the following formulation was produced.

| | | (mass %) |
|---|---|---|
| A | candelilla wax | 8.00 |
| | paraffin | 6.00 |
| | beeswax | 3.00 |
| | Carnauba wax | 2.00 |
| | lanolin | 7.17 |
| | castor oil | 16.30 |
| | cetyl ethylhexanoate | 13.03 |
| | ethyl palmitatehexyl | 10.32 |
| | hydrogenated polyisobutene | 5.00 |
| B | Red 202 | 1.05 |
| | yellow 4 | 0.90 |
| | Blue 1 | 0.04 |
| | titanium oxide | 1.60 |
| | diisostearyl malate | 3.59 |
| C | mica, titanium oxide | 1.00 |
| | mica | 1.00 |
| D | phytosteryl/octyldodecyl lauroyl glutamate | balance |
| | compound of Synthetic Example 1 (decanoyl proline) | 0.10 |
| | total | 100 |

Preparation method: Component A was dissolved by heating, component B mixture was added, and the mixture was kneaded in a roll mill to give a uniform dispersion. Furthermore, component C and component D were added, and the mixture was defoamed, poured into a mold and rapidly cooled to give a lip stick.

Formulation Example 14

Hair Conditioner

A hair conditioner having the following formulation was produced.

| | | (mass %) |
|---|---|---|
| A | stearyl alcohol | 5.00 |
| | phytosteryl/octyldodecyl lauroyl glutamate | 3.00 |
| | dimethicone | 2.00 |
| | glyceryl stearate | 0.50 |
| | triisostearic acid PEG-20 hydrogenated castor oil | 1.00 |
| B | behentrimonium chloride | 4.00 |
| | glycerol | 5.00 |
| | methylparaben | 0.10 |
| | arginine | 0.10 |
| | amodimethicone (40% aqueous solution) | 2.50 |
| | water | balance |
| | compound of Synthetic Example 2 (decanoyl proline Na) | 0.20 |
| | etidronate | 0.01 |
| | total | 100 |

Preparation method: Component A and component B were respectively heated to 80° C., component A was gradually added to stirring component B, and the mixture was cooled to room temperature.

Formulation Example 15

Hair Cream

A hair cream having the following formulation was produced.

| | | (mass %) |
|---|---|---|
| A | liquid paraffin | 38.00 |
| | petrolatum | 7.00 |
| | beeswax | 2.00 |
| | phytosteryl/octyldodecyl lauroyl glutamate | 2.00 |
| | stearic acid PEG-3 | 2.70 |
| | oleth-6 | 2.30 |
| | ceteth-7 | 3.00 |
| | propylparaben | 0.10 |
| B | methylparaben | 0.10 |
| | sodium stearoyl glutamate | 0.50 |
| | water | balance |
| | compound of Synthetic Example 2 (decanoyl proline Na) | 0.20 |
| | etidronate | 0.01 |
| | total | 100 |

Preparation method: Component A and component B were respectively heated to 70° C., component B was gradually added to stirring component A, and the mixture was cooled to room temperature.

Formulation Example 16

Cleansing Oil

A cleansing oil having the following formulation was produced.

| | | (mass %) |
|---|---|---|
| A | liquid paraffin | balance |
| | phytosteryl/octyldodecyl lauroyl glutamate | 5.00 |
| | phenyl trimethicone | 15.00 |
| | palm kernel fatty acid amide DEA | 0.50 |
| | diisostearic acid PEG-8 | 1.00 |
| | diisostearic acid PEG-12 | 8.00 |
| | cetyl octanoate | 20.00 |
| | isostearic acid PEG-10 | 2.00 |
| | isostearic acid | 0.40 |
| | tocopherol | 0.10 |
| | flavor | q.s. |
| B | ethanol | 1.00 |
| | propanediol | 0.50 |
| | water | 1.50 |
| | compound of Synthetic Example 2 (decanoyl proline Na) | 0.10 |
| | etidronate | 0.01 |
| | total | 100.00 |

Preparation method: Component A and component B were dissolved at room temperature, and component B was gradually added to stirring component A.

Formulation Example 17

Washable Cleansing Oil

A washable cleansing oil having the following formulation was produced.

| | | (mass %) |
|---|---|---|
| A | cetyl octanoate | 13.00 |
| | hexyldecanol | 1.00 |
| | isostearic acid | 2.50 |
| | phytosteryl/octyldodecyl lauroyl glutamate | 3.50 |
| | cyclomethicone | 10.00 |
| | diisostearic acid PEG-12 | 3.00 |
| | PEG-20 glyceryl diisostearate | 17.00 |
| B | methyl gluceth-10 | 2.00 |
| | DPG | 18.00 |
| | methylparaben | 0.10 |
| | water | balance |
| | compound of Synthetic Example 2 (decanoyl proline Na) | 0.10 |
| | etidronate | 0.01 |
| | total | 100.00 |

Preparation method: Component A and component B were heated to 60° C., and component B was gradually added to stirring component A.

Formulation Example 18

Cleansing Gel

A cleansing gel having the following formulation was produced.

| | | (mass %) |
|---|---|---|
| A | cetyl octanoate | balance |
| | isononyl isononanoate | 10.00 |
| | phytosteryl/octyldodecyl lauroyl glutamate | 10.00 |
| | olive oil | 10.00 |
| | trioctanoin | 5.00 |
| | PEG-20 glyceryl triisostearate | 2.00 |
| | jojoba oil | 1.00 |
| | macadamia nut oil | 1.50 |
| | phenoxyethanol | 0.40 |
| | bisabolol | 0.10 |
| B | urea | 1.50 |
| | sorbitol (70% aqueous solution) | 3.00 |
| | glycerol | 7.00 |
| C | palm kernel fatty acid amide DEA | 0.50 |
| | glycereth-25 PCA isostearate | 3.00 |
| | PEG-60 hydrogenated castor oil | 5.00 |
| | compound of Synthetic Example 1 (decanoyl proline) | 0.10 |
| | total | 100.00 |

Preparation method: Component A and component B were dissolved by stirring at room temperature, and component C was added to component B. This was added to stirring component A.

Formulation Example 19

Hair Shampoo

A hair shampoo having the following formulation was produced.

| | | (mass %) |
|---|---|---|
| A | sodium laureth sulfate (27%) | 30.00 |
| | Cocamide propylbetaine (30%) | 15.00 |
| | pentyleneglycol | 2.00 |
| | Glyceryl caprylate | 1.00 |
| | Polysorbate 85 | 1.00 |
| | triisostearic acid PEG-160 sorbitan | 1.00 |
| | Polyquaternium-10 | 0.20 |
| | phytosteryl/octyldodecyl lauroyl glutamate | 0.50 |
| | water | balance |
| B | compound of Synthetic Example 2 (decanoyl proline Na) | 0.20 |
| | citric acid (10% aqueous solution) | q.s. |
| | water | 5.00 |
| | methylisothiazolinone | 0.01 |
| | methylchloroisothiazolinone | 0.01 |
| | sodium benzoate | 0.05 |
| | total | 100.00 |

Preparation method: Component A was dissolved by stirring at 80° C. and cooled, and component B was added to give the shampoo.

The samples and reagents used were as follows.
etidronate: added as etidronic acid: 1-hydroxyethane-1,1-diphosphonic acid (manufactured by Tokyo Chemical Industry Co., Ltd.)
betaine: aminocoat (manufactured by Asahi Kasei Corporation)
sodium lactate: sodium lactate (manufactured by Wako Pure Chemical Industries, Ltd.)
sodium pyrrolidonecarboxylate: "AJIDEW" NL-50 (manufactured by Ajinomoto Co., Inc.)
glycerol: concentrated glycerin (manufactured by Kao Corporation)
sorbitol: sorbitol (manufactured by Kao Corporation)
squalane: squalane (manufactured by Maruha Nichiro Corporation)
jojoba oil: purified jojoba oil (manufactured by KOEI KOGYO Co., Ltd.)
glyceryl stearate: NIKKOL GMS-BV2 (manufactured by Nikko Chemicals)
sucrose palmitate: surfhope SE COSME C-1615 (manufactured by Mitsubishi-Kagaku Foods Corporation)
sodium stearoyl glutamate: "Amisoft" HS-11P (manufactured by Ajinomoto Co., Inc.)
acetylproline: acetylproline (manufactured by WATANABE CHEMICAL INDUSTRIES, LTD.)
acetylglutamate: N-acetyl-L-glutamate (manufactured by Tokyo Chemical Industry Co., Ltd.)
EDTA: EDTA-2Na (manufactured by Wako Pure Chemical Industries, Ltd.)
sodium hyaluronate: FCH-120 (manufactured by Food Chemifa Co., Ltd.)
phytosteryl/octyldodecyl lauroyl glutamate: "Eldew" PS-203 (manufactured by Ajinomoto Co., Inc.)
cetyl octanoate: CEH (manufactured by Kokyu Alcohol Kogyo Co., Ltd.)
PPG-8 ceteth 20: NIKKOL PBC-44 (manufactured by Nikko Chemicals)

PPG-6 DECYLTETRADECETH 30: NIKKOL PEN-4630 (manufactured by Nikko Chemicals)

DPG: DPG-RF (manufactured by ADEKA)

BG: 1,3-BG UK (manufactured by Daicel Chemical Industries, Ltd.)

cocoylglycine Na: "AMILITE" GCK-12K (manufactured by Ajinomoto Co., Inc.)

lauramidepropylbetaine: Softazoline LPB (manufactured by Kawaken Fine Chemicals Co., Ltd.)

glyceryl caprylate: Sunsoft No.760 (manufactured by Taiyo Chemical Industry Co., Ltd.)

hydroxypropylstarchphosphoric acid: STRUCTURE XL (manufactured by Akzo Nobel)

PEG-9 polydimethylsiloxyethyl dimethicone: KF-6028 (manufactured by Shin-Etsu Chemical Co., Ltd.)

quaternium 18 hectorite: Lucentite SAN (manufactured by CO-OP CHEMICAL CO., LTD.)

PEG-10 dimethicone: KF-6017 (manufactured by Shin-Etsu Chemical Co., Ltd.)

PEG-15 glyceryl isostearate: EMALEX GWIS-155 (manufactured by Nihon Emulsion Co., Ltd.)

hydrogenated lecithin: NIKKOL Lecinol S-10 (manufactured by Nikko Chemicals)

(vinyldimethicone/methicone silsesquioxane)crosspolymer: KSP-100 (manufactured by Shin-Etsu Chemical Co., Ltd.)

(dimethicone/(PEG-10/15))crosspolymer: KSG-210 (manufactured by Shin-Etsu Chemical Co., Ltd.)

oleth-6: EMALEX 506 (manufactured by Nihon Emulsion Co., Ltd.)

ceteth-7: EMALEX 107 (manufactured by Nihon Emulsion Co., Ltd.)

methyl gluceth-10: MACBIOBRIDE MG-10E (manufactured by NOF CORPORATION)

INDUSTRIAL APPLICABILITY

According to the present invention, a moisturizer having hygroscopicity and water retention ability can be provided. Using the moisturizer, a composition superior in antiseptic property and feeling on application, in addition to moisturizing property, and free of coloration and odorizationcan be provided. The moisturizer and the composition can be used as cosmetic agents.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A moisturizer comprising an acylproline of formula (1) or a salt thereof

wherein an acyl group represented by $R^1$—CO— is an acyl group of a saturated or unsaturated fatty acid having 6 to 14 carbon atoms.

2. The moisturizer according to claim 1, wherein said acyl group is selected from the group consisting of a hexanoyl group, a heptanoyl group, an octanoyl group, a tert-octanoyl group, a 2-ethylhexanoyl group, a nonanoyl group, an isononanoyl group, a decanoyl group, an isodecanoyl group, an undecanoyl group, a lauroyl group, a myristoyl group, and an undecylenoyl group.

3. The moisturizer according to claim 1, wherein said acylproline is decanoyl proline or a salt thereof.

4. The moisturizer according to claim 1, wherein said acylproline of formula (1) or a salt thereof is a sodium salt of an acylproline of formula (1).

5. A composition comprising (A) an acylproline of formula (1) or a salt thereof

wherein an acyl group represented by $R^1$—CO— is an acyl group of a saturated or unsaturated fatty acid having 3 to 23 carbon atoms, and (B) a bisphosphonate.

6. The composition according to claim 5, wherein the acyl group represented by $R^1$—CO— is an acyl group of a saturated or unsaturated fatty acid having 6 to 14 carbon atoms.

7. The composition according to claim 5, wherein said acylproline is decanoyl proline or a salt thereof.

8. The composition according to claim 5, wherein said acylproline of formula (1) or a salt thereof is a sodium salt of an acylproline of formula (1).

9. The composition according to claim 5, wherein (B) is etidronate.

10. The composition according to claim 9, wherein etidronate is added thereto in the form of etidronic acid.

11. The composition according to claim 5, wherein the weight ratio of (A) to (B) ((A)/(B)) ranges from 100,000 to 3.

12. The composition according to claim 5, wherein (A) is present in an amount ranging from 0.001 wt % to 40 wt %.

13. The composition according to claim 5, wherein (B) is present in an amount ranging from 0.00001 wt % to 5 wt %.

14. The composition according to claim 5, further comprising
(C) an alcohol having 6 to 24 carbon atoms.

15. The composition according to claim 14, wherein said alcohol is selected from the group consisting of lauryl alcohol, myristyl alcohol, cetyl alcohol, stearyl alcohol, behenyl alcohol, isostearyl alcohol, and octyldodecanol.

16. The composition according to claim 14, wherein (C) is present in an amount ranging from 0.01 wt % to 20 wt %.

17. The composition according to claim 5, wherein said composition further comprises at least one additional component selected from the group consisting of an oil solution, a chelating agent, a surfactant, a powder, an amino acid, a polyamino acid, a salt of a polyamino acid, a sugar alcohol, an alkylene oxide adduct of a sugar alcohol, a lower alcohol, an animal extract, a plant extract, a nucleic acid, a vitamin, an enzyme, an anti-inflammatory agent, an antimicrobial agent, a preservative, an antioxidant, a UV absorber, an adiaphoretic, a pigment, a dye, an oxidation dye, an organic powder, an inorganic powder, a pH adjuster, a pearly sheen agent, and a wetting agent.

18. A method for suppressing decomposition of acylproline of formula (1) or a salt thereof:

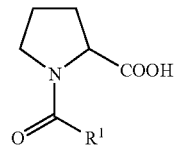

(1)

wherein an acyl group represented by $R^1$—CO— is an acyl group of a saturated or unsaturated fatty acid having 3 to 23 carbon atoms, wherein said method comprises adding a bisphosphonate to said acylproline of formula (1) or a salt thereof.

19. A moisturizing method comprising topically applying to the skin of a subject an effective amount of an acylproline of formula (1) or a salt thereof:

(1)

wherein an acyl group represented by $R^1$—CO— is an acyl group of a saturated or unsaturated fatty acid having 3 to 23 carbon atoms.

20. A moisturizing method comprising topically applying to the skin of a subject an effective amount of a composition comprising
(A) an acylproline of formula (1) or a salt thereof:

(1)

wherein an acyl group represented by $R^1$—CO— is an acyl group of a saturated or unsaturated fatty acid having 3 to 23 carbon atoms, and
(B) a bisphosphonate.

* * * * *